(12) United States Patent
Kaye et al.

(10) Patent No.: US 7,436,515 B2
(45) Date of Patent: Oct. 14, 2008

(54) FLUID BORNE PARTICLE ANALYZERS

(75) Inventors: Paul Henry Kaye, Kimpton (GB); Edwin Hirst, Hemel Hempstead (GB)

(73) Assignee: The Secretary of State of Defense, DSTL, Salisbury (GB)

( * ) Notice: Subject to any disclaimer, the term of this patent is extended or adjusted under 35 U.S.C. 154(b) by 195 days.

(21) Appl. No.: 11/314,972

(22) Filed: Dec. 21, 2005

(65) Prior Publication Data
US 2006/0250606 A1 Nov. 9, 2006

(30) Foreign Application Priority Data

| Jun. 26, 2003 | (GB) | ................................. 0314850.9 |
| Apr. 23, 2004 | (GB) | ................................. 0409090.8 |
| Jun. 28, 2004 | (WO) | ............... PCT/GB2004/002761 |

(51) Int. Cl.
*G01N 21/00* (2006.01)
(52) U.S. Cl. ...................................... 356/436; 356/441
(58) Field of Classification Search ................. 356/311, 356/317, 318, 337–343, 436–442; 250/373, 250/343, 228, 428, 432 R, 435, 458.1, 461.1, 250/459.1; 422/82.05, 82.08, 82.09; 436/171–172
See application file for complete search history.

(56) References Cited

U.S. PATENT DOCUMENTS

| 5,047,846 | A | | 9/1991 | Uchiyama et al. |
| 5,347,138 | A | * | 9/1994 | Aqui et al. .................. 250/573 |
| 5,713,364 | A | * | 2/1998 | DeBaryshe et al. ......... 600/476 |
| 5,772,769 | A | * | 6/1998 | Sayka ......................... 118/712 |
| 6,080,584 | A | | 6/2000 | Alfano et al. |
| 6,091,985 | A | | 7/2000 | Alfano et al. |
| 7,075,646 | B2 | * | 7/2006 | Cole .......................... 356/338 |
| 2004/0159799 | A1 | * | 8/2004 | Saccomanno ............ 250/461.1 |

FOREIGN PATENT DOCUMENTS

| EP | 0414237 A2 | 5/1997 |
| JP | 03024442 | 2/1991 |
| JP | 10096697 | 4/1998 |
| JP | 2000325294 | 11/2000 |
| JP | 2002125696 | 5/2002 |
| WO | 99/17086 A1 | 4/1999 |

OTHER PUBLICATIONS

Dr. E. P. Plummer, Search Report under Section 17, The Patent Office, Great Britain, searched Jun. 21, 2007.

* cited by examiner

*Primary Examiner*—Gregory J Toatley, Jr.
*Assistant Examiner*—Tri T Ton
(74) *Attorney, Agent, or Firm*—Bradley N. Ruben (57) ABSTRACT

This invention describes an improved method and apparatus for the analysis of fluid borne particles and which is especially suitable for the detection of airborne biological particles. In one aspect of the invention provides an apparatus for the detection of fluid borne particles which comprises a zone through which a fluid to be analyzed flows in use, a source of illumination to illuminate/irradiate fluid borne particles present in said zone, and a detector to detect light from the particles as an indicator of the presence or characteristics of the particles, wherein the apparatus comprises an integrating sphere and the zone is within the integrating sphere. The apparatus is highly sensitive and can be used for detecting airborne particles even where the particles are present at very low particle concentrations in the air.

34 Claims, 4 Drawing Sheets

FLUID BORNE PARTICLE ANALYZERS

FIELD OF THE INVENTION

The present invention concerns improvements in and relating to analyzers for fluid borne particles, e.g. analyzers for detecting or determining characteristics of biological particles such as bacterial cells present in a sample of air.

BACKGROUND TO THE INVENTION

In a wide variety of environmental, occupational, military and industrial scenarios, fine particles, typically within the size range from a few tenths of a micrometer to a few hundred micrometers, play an important role. Environmental airborne particles, usually comprising mineral dusts, combustion products and biological particles, which are carried by winds and other air movement, can result in breathing difficulties, allergic reactions a possible degradation of the body's immune system. Occupational particles can contaminate industrial products and processes and can also present a respirable health hazard, such as in the case of asbestos fibres or fugitive pharmaceutical powder particles. In the military field, the deliberate generation of hazardous aerosols has posed a major threat since their first substantial use in World War I, and today a wide variety of biological and chemical weapons are believed to be possessed by both national governments and terrorist organisations.

The in-situ characterization of airborne particles has therefore become an important objective in both civilian and military fields, and considerable effort has gone into developing techniques which can analyze certain particle parameters and provide some degree of identification or classification. Moreover, since even brief exposure to some of the aforementioned aerosols can damage health and may even prove fatal, the speed of response of the measurement technique has been an important consideration.

A potentially powerful technique of airborne particle analysis involves the introduction of individual particles into a near vacuum where they are fragmented using an intense laser light pulse. The resulting atomic and molecular fragments are then measured using a time-of-flight mass spectrometer or similar, yielding a detailed assessment of the material content of the particle. (See for example, Marijnissen J et al, "Proposed on-line aerosol analysis combining size determination, laser induced fragmentation, and time-of-flight mass specrometry", Journal of Aerosol Science, volume 19, pages 1307-1310, 1988). Such methods offer a high degree of particle discrimination but remain expensive and cumbersome to implement and, because they are comparatively slow in terms of the rate at which individual particles can be analyzed, they do not offer the real-time aerosol analysis capability (ie: response to a change in aerosol composition within a few seconds) desired in monitoring applications.

Of other possible particle characterization techniques, those based on elastic optical scattering have become popular because they offer genuine real-time non-destructive particle analysis. Here, the term elastic denotes that the scattered light is at the same wavelength as the illuminating light. In their simplest form, optical scattering instruments are designed to draw ambient airborne particles through a measurement space. A light source, usually a laser, illuminates the measurement space and the particles scatter some radiation to an appropriately positioned detector. The magnitude of the scattered radiation may, to a first order, be used to determine a particle sizes and number illuminated at any instant. Whilst comparatively straightforward to implement, simple light scattering techniques such as these do not yield sufficient information about the particles to provide anything other than a very superficial overview of the ambient aerosol. They do not, for example, provide any indication of the material nature of the particles; whether the particles are of solid or liquid form; or whether the particles are of biological or non-biological origin.

In order to discriminate more effectively between airborne particles of different types, a number of methods have been developed which measure multiple parameters from individual particles in addition to their (optical scattering) size. For example, analysis of the spatial distribution of light scattered by individual airborne particles passing through the measurement space of an optical scattering instrument has proved to be an effective method of improving particle discrimination. This is because the spatial pattern or scattered light contains information relating to the shape of the scattering particle. Examples of instrument geometries which embody this approach to spatial scattering analysis are described in: 'Portable Particle Analysers', Ludlow, I. K. and Kaye P H. European Patent EP 0 316 172, Jul. 1992; 'Particle Asymmetry Analyser', Ludlow, I. K. and Kaye, P. H. European Patent EP 0 316 171, Sept. 1992.; 'Apparatus and Method for the Analysis of Particle Characteristics using Monotonically Scattered Light', Kaye, P.H. and Hirst, E. U.S. Pat. No. 5,471,299, Nov. 28, 1995; and 'Hazardous Airborne Fibre Detector'. Hirst E. and Kaye, P.H. UK Patent Application No: 9619242.2; filed 14th Sep. 1996. These may be considered as prior art.

However, light scattering analysis instruments of the type described above cannot discriminate particles on the basis of their material structure. For example, a non-biological silicate-based particle may yield an essentially identical spatial scattering pattern to a biological cell of similar size and shape. In order to discriminate particles on the basis of their material structure it is necessary to employ other techniques such as an analysis of light which is scattered inelastically by the particle. Such light is manifest as either a fluorescence emission or, far more weakly, a Raman emission. Since useful Raman signals from individual microscopic particles in flow have, to date, proved unattainable, they will not be discussed further here. In contrast, several workers have demonstrated successful measurement of fluorescent spectra from single airborne particles and have used this technique to attempt particle discrimination on the basis of fluorescence. For example, Pinnick et al ('Fluorescent Particle Counter for Detecting Airborne Bacteria and Other Biological Particles' Pinnick R G et al., Aerosol Science and Technology, volume 23, pages 653-664, 1995) developed an instrument in which a stream of airborne particles passes through a measurement space and is illuminated with light at 488 nm wavelength from an Argonion laser. The light excites some naturally occurring fluorophores within the particles and the fluorescence emission spectrum between 500 nm and 800 nm wavelength is recorded and analysed. Based on the fact that biological particles such as spores produced measurable fluorescence, the authors proposed the technique as a possible means of discriminating biological from other non-biological particles that may be present in an environment. Other workers, (for example see Hairston P P et al, "Design of an instrument for real-time detection of bioaerosols using simultaneous measurement of particle aerodynamic size and intrinsic fluorescence", Journal of Aerosol Science, vol. 28, no. 3, pages 471-482, 1997), have combined a measurement of the magnitude of fluorescence from a particle with a measure of its size, in this case the aerodynamic size of the particle. This dual-parameter measurement approach provides a greater degree of particle discrimination than measurement of particle fluorescence alone. This method has been extended by Kaye P H et al. "Simultaneous light scattering and intrinsic fluorescence measurement for the classification of airborne particles U", Applied Optics, volume 39, number 21, pp 3738-3745, to incorporate a method of determining the shape of individual particles from an analysis to the spatial distribution of light scattered by the particle. These methods too may be considered prior art.

However, all of the methods described above involve the analysis of individual particles at normally high processing rates. Whilst offering a high degree of particle discrimination, the methods all suffer the same problem of being expensive and complex to implement. This high cost is a result of the requirement for an intense and well-collimated light source, usually a laser, the requirement for precision optical systems, the need for complex and high-speed data processing electronics, and, normally, the need for an independent power generator to supply the instruments with electrical power over extended time periods. Because of the high cost of implementing the methods, the deployment of monitors based on them is normally limited to very small numbers of discrete monitors. In some cases, especially outdoor environments or areas of military conflict, the biological threat may appear anywhere across a large area, and the deployment of small number of discrete monitors is of limited value in rapidly detecting the threat, should it arise. What is required, therefore, is a monitor which is of sufficiently low cost and small size that it may be manufactured and deployed in very large numbers across wide areas of potential risk, or even that it could be worn or carried by every individual person in the area who may be exposed to the biological hazard. Such a monitor would ideally meet the following specification:

1. Low cost.
2. Hand portable or person wearable.
3. No reagent requirement. (i.e: no requirement for recharging chemical or biochemical assay systems).
4. Unattended operation.
5. Typically 48 to 72 hours continuous operation using built-in battery power supply or similar.
6. Maximum response time of typically 10s. i.e: will detect the presence of biological particles in an environment within a time period short enough to prevent significant exposure of individuals to the hazard.

A detector which meets this specification is described in the present applicant's earlier UK patent application 0210116.0 'Detector for airborne biological particles', which may be considered prior art.

The detector described in UK patent application 0210116.0 'Detector for airborne biological particles', operates by drawing a continuous flow of ambient air through a chamber, periodically illuminating this air with ultraviolet light, and measuring the magnitude of scattered light and fluorescence emission from the particles suspended in the air. The relationship between the scatter and fluorescent signals is indicative of the presence or absence of biological particles in the air sample.

A potential drawback of this type of detector relates to the size of the volume of the illuminated air parcel (referred to as the 'scattering volume'). With low particle number concentrations in the air, it could be possible for no particles to be present in the scattering volume and therefore for no signal to be recorded. Equally, if only a small number of particles is present in the scattering volume, the magnitude of the recorded scatter and fluorescence light signals may be too low for accurate measurement, primarily because the scatter and fluorescent light emanates from the particles in all directions and yet is collected over only a small fraction (typically ~10% of the total).

It is an object of the present invention amongst others to overcome these limitations and offer substantial improvement in detection sensitivity over the prior art. Further objects include obtaining further economies in cost of the apparatus, with enhancements to the apparatus to provide for useful characterization of contaminant particles despite a relatively low cost construction.

SUMMARY OF THE INVENTION

According to a first aspect of the present invention there is provided an apparatus for the detection of fluid borne particles which comprises:

a zone through which a fluid to be analyzed flows, in use;
a source of illumination to illuminate/irradiate fluid borne particles present in said zone; and
a detector to detect light from the particles as an indicator of the presence or characteristics of the particles, wherein the apparatus comprises a pair of opposed concave reflective surfaces and the zone is between these surfaces, the apparatus having two sources and two detectors, the first of the two detectors detecting a first wavelength band and the second of the detectors detecting a second wavelength band that is narrower than the first band and falls within the first band, the first source illuminating/irradiating within a wavelength band that is below the wavelength detecting band of the first detector but within the wavelength detecting band of the second detector.

Preferably the first of the two detectors detects a wavelength band of about 340 to about 600 nm and the second detector detects a band of 410 to 600 nm, the first source has a wavelength band of about 260 to about 290 nm.

Suitably the second source has a wavelength band of about 340 to about 380 nm.

In a preferred embodiment the first and second detectors are arranged along a first axis and the first and second source are arranged along a second axis substantially orthogonal to the first axis. Preferably the fluid flow is along a third axis substantially orthogonal to the first and second axes.

The apparatus preferably comprises a pair of opposed concave reflective surfaces and the zone is between these surfaces.

Suitably the apparatus is an apparatus for the detection of fluid borne particles which comprises:

a zone through which a fluid to be analyzed flows, in use;
a source of illumination to illuminate/irradiate fluid borne particles present in said zone; and
a detector to detect light from the particles as an indicator of the presence or characteristics of the particles, wherein the apparatus comprises a pair of opposed concave reflective surfaces and the zone is between these surfaces.

Each of the pair of opposed substantially concave reflective surfaces may comprise a respective discrete mirror or the apparatus may comprise an integrating sphere wherein the pair of opposed concave reflective surfaces are reflective surfaces of the integrating sphere.

For the integrating sphere embodiment, particularly preferably the reflective internal spherical surface of the integrating sphere is specular/diffusing in nature.

The provision of an integrating sphere within which the test aerosol flows and is illuminated dramatically enhances sensitivity. The integrating sphere not only allows a proportionally larger scattering volume to be implemented, therefore retaining detection sensitivity even for low particle concentrations, but also acts as a very efficient collector of scattered and fluorescence radiation emanating from any airborne particles under examination, thus maximising the opportunity for using a combination of scatter and fluorescence signals in discriminating the types of particles present in the aerosol.

Particularly preferably the apparatus is configured so that the fluid to be analyzed flows through the integrating sphere along a flow path and the illumination/irradiation source is directed along the flow path whereby the illuminations/irradiation and the fluid enter the integrating sphere by a common aperture. By the use of at least a common entry aperture into the integrating sphere for both the fluid and the illumination/irradiation the number/area of apertures that would otherwise undermine the sensitivity of the apparatus is minimized.

Preferably the fluid is constrained to flow through a transparent tube, the tube being substantially transparent to the illumination/irradiation used and extending through the sphere. Suitably the tube is a quartz tube.

Preferably the apparatus further comprises an optically absorbing beam-dump at the distal end of the tube to absorb the illumination/irradiation beam. Preferably the apparatus incorporates a detector at the distal end of the tube to measure the energy/power of the illumination/irradiation beam.

Where the illumination/irradiation is directed along the tube as a beam, the diameter of the beam is advantageously such that the beam fills most of the tube without coming into contact with the tube walls, thus avoiding scattering from particles that may have deposited on the walls.

According to a second aspect of the present invention there is provided an apparatus for the detection of fluid borne particles which comprises:

a zone through which a fluid to be analyzed flows, in use;

a source of illumination to illuminate/irradiate fluid borne particles present in said zone: and a detector to detect light fluoresced from the particles as an indicator of the presence or characteristics of the particles, wherein the apparatus comprises a pair of substantially coaxially opposed substantially spherical mirrors to collect fluoresced light and wherein the zone is defined between the substantially spherical mirrors.

Advantageously, each respective substantially spherical mirror has a central aperture and has a respective detector to detect light received through the aperture from the other mirror.

Preferably the axis linking the centers of the opposed substantially spherical mirrors is substantially orthogonal to an axis of illumination from the source of illumination.

Preferably the apparatus is adapted to provide two or more different sources of illumination. In one preferred embodiment the at least two sources of illumination comprise two xenon sources each emitting a different wavelength band of light to the other. Suitably the different light sources are spatially distinct from each other. They may alternatively comprise a single light source element and which is switchable between different wavelength bands of emission. The light source element(s) suitably is/are xenon light source elements having a low pass filter between the source and the zone to allow only the lower wavelengths that are in the appropriate range to excite fluorescence to pass. Suitably the filter only allows radiation at or under about 370 nanometers to pass. In one preferred embodiment there are two xenon light source elements and each has a different respective filter suitably one light source element/filter combination emits light up to about 290 nanometers and the other emits light from above 290 nanometers suitably to about 380 nanometers.

Preferably where two spatially discrete light sources are provided, these are spaced apart in a configuration each along an axis wherein the axis is orthogonal to the axis linking the detectors. Furthermore, suitably the axis linking the detectors is substantially aligned with an axis linking the centers of each of the opposed spherical mirrors. For the avoidance of doubt, the expression "spherical mirror" refers to a concave mirror of which the surface is formed with a curvature that is that of a sphere.

Preferably the apparatus of the invention further comprises a processor configured to operate the apparatus in a manner whereby the source of illumination alternately changes between two or more different band widths of wavelength. Suitably the processor is further programmed to process signals sensed from the one or more detectors to provide a ratio of sensed signal for one wavelength or wavelength band of illuminating light relative to sensed signal for a different wavelength or band of wavelength of illuminating light and further suitably does so at each of two or more different sensed wavelengths or bands of wavelength of detected fluorescence signal. The apparatus suitably has two or more detectors each with a different wavelength pass/bandpass.

In a further aspect of the present invention there is provided a method for the detection of fluid borne particles comprising the provision of an apparatus substantially of the first or second aspects of the present invention with or without an integrating sphere or spherical mirrors and wherein the method comprises alternately illuminating a said zone with different wavelength bandwidths of light to elicit different wavelengths of fluorescent radiation from any biological particles in said zone and monitoring for the different bandwidth wavelengths of fluorescence elicited and obtaining a ratio of the sensed signal for wavelength or wavelength band of illuminating light relative to a corresponding signal for another wavelength or wavelength band of illuminating light as a means of facilitating characterizing of any biological particles within the zone.

In all embodiments of apparatus it is preferred that the source of illumination is xenon or a similar low cost source of illumination. However, In one preferred alternative embodiment the source of illumination might comprise a short wavelength/UV diode laser. In one example, a 370 nanometer laser emitting diode might be used.

BRIEF DESCRIPTION OF THE DRAWINGS

A preferred embodiment of the first aspect of the present invention is shown in FIG. 1 of the accompanying drawings which comprises a part-sectional schematic diagram of an airborne particle analyser for detecting and/or characterizing airborne biological particles such as bacterial cells, the analyser having an integrating sphere.

A preferred embodiment of the second aspect of the present invention is then shown in FIGS. 2 to 4, wherein.

DESCRIPTION OF PREFERRED EMBODIMENT

Figure 1:
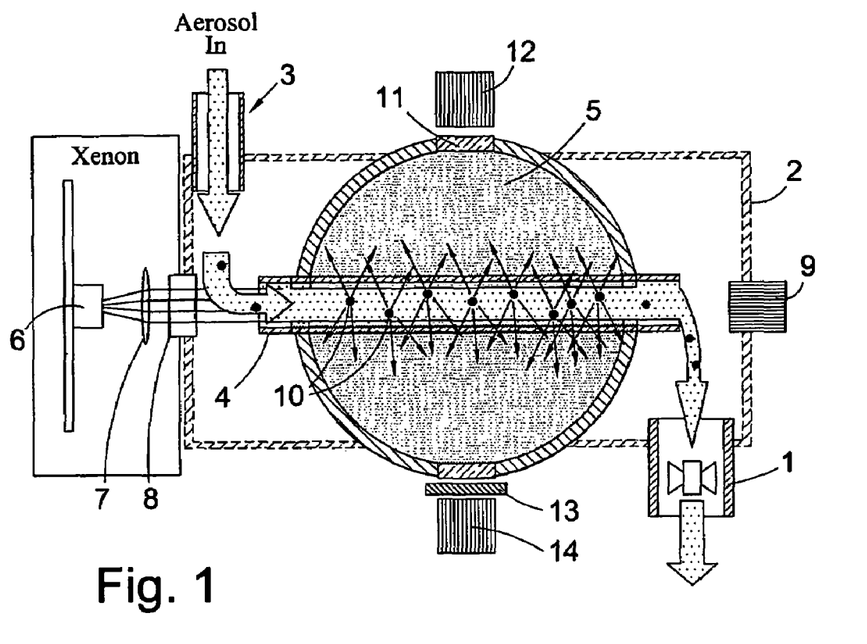

Ambient aerosol (air containing suspended particles) is drawn by an electrical fan 1 into a sealed enclosure 2 through an inlet pipe 3. When inside the enclosure 2, the aerosol is forced to pass through a quartz tube 4 whose axis lies along the diameter of an integrating sphere 5. (Integrating spheres are normally employed to measure the total light output of radiation sources such as light emitting diodes or incandescent lamps. They comprise a spherical container whose internal surface is coated with a material of very high diffuse reflectivity, typically greater than 98%. The sphere has the property that light radiating from any isotropic point-source in the sphere will undergo multiple diffuse reflections from the sphere surface such that the radiation flux striking the surface becomes essentially equal over the entire sphere surface area. If a small window is made in the sphere surface, the light will pass out through this window. Theoretical analysis of integrating sphere behaviour shows that the amount of light passing through the window is significantly greater than would occur if there was no sphere present but instead the window was in a plane opaque surface perpendicular to the axis between the point-source and the window. (See for example, 'Integrating Sphere Theory and Applications', Technical Information, Labsphere Inc., 231 Shaker Street, P.O. Box 70, North Sutton, N.H. 03260, USA). This optical 'gain' is referred to as the 'sphere multiplier', and may be of value ~10 to 50 depending on the reflectivity of the sphere surface and the proportion of the surface area occupied by the window. In essence, therefore, the sphere integrates the light emanating from the point-source over all directions, and ultimately delivers the majority of this light to the window. If therefore, an optical detector is placed at the window, the output of the detector will be significantly greater than would be the case with no sphere present).

A radiation source such as a xenon discharge tube 6 provides pulses of ultraviolet radiation at typically 0.5 second intervals. The radiation passes through collimating optics 7 and an optical filter 8, the latter selected such that the wavelength band transmitted corresponds to that required to cause fluorescence of one of the molecular constituents commonly found in biological cells. For example, Tryptophan is optimally excited by wavelengths in the 250-280 nm wavelength band, whilst NADH (Nicotinamide adenine dinucleotide) is optimally excited by wavelengths in the 340-370 nm range. The radiation then passes axially along the quartz tube 4. The diameter of the collimated UV beam is such that the pulsed beam fills most of the tube without coming into contact with the tube walls (thus avoiding scattering from particles that may have deposited on the walls). At the far end of the quartz tube, the UV pulsed beam is terminated in an optically absorbing beam-dump 9 which also incorporates a detector to measure the energy of the UV pulse.

Particles 10 suspended in the airstream passing through the quartz tube are therefore periodically illuminated with ultraviolet radiation. The air flow-rate through the tube is arranged such that normally the parcel of air is completely replaced between pulses of UV radiation. (On occasion, this may not be the case, as described below). The illuminated particles scatter the UV radiation in all directions, the magnitude of the scattering being related to each particle's size. The particles may also fluoresce, and the fluorescence emission will again normally be in all directions. The UV scattered radiation and the longer wavelength fluorescence radiation pass through the walls of the quartz tube and into the integrating sphere.

The integrating sphere has two or more small windows. At the first window 11 is an optical detector 12 such as a photomultiplier or avalanche photodiode capable of detecting and measuring the flux of scattered UV light within the sphere. At a second window 12 is an optical filter 13 which blocks the scattered UV light and only allows the longer wavelength fluorescence radiation to pass through to a second optical detector 14. The outputs from the two detectors 12 and 14 are therefore a measure of the number and sizes of particles carried within the quartz tube 4 and of the presence of biological fluorophores within those particles, respectively. These output values are normalized to the UV pulse energy measured by the detector 9, so as to avoid errors which could arise from pulse-to-pulse energy variation.

In a second embodiment of the invention, the optical filter 8 is replaced by a set of filters supported in, for example, a rotating filter-wheel, such that successive pulses of radiation from the xenon source 6 are filtered to transmit a succession of different wavelength bands. If, for example, the filter wheel held three filters, then the xenon would be triggered to produce three pulses in rapid succession, followed by a gap of ~0.5 seconds. Thus the particles suspended within the quartz tube 4 would sequentially be illuminated at three different wavelength bands, and the outputs recorded from the fluorescence detector 14 would reflect the degree to which specific biological fluorophores such as Tryptophan or NADH were present. This information would significantly enhance the ability of the invention to discriminate various types of biological particles in the air.

In a third embodiment of the invention, the number of 'fluorescence detector' windows 12 could be increase to typically three or four, with each having a different optical filter. In this way, the spectral distribution of fluorescence radiation emanating from the illuminated particles could be measured. This would further enhance the ability of the invention to discriminate various types of biological particles in the air. (A drawback of implementing additional windows in the integrating sphere is that the 'sphere multiplier' will decrease, thus reducing the 'optical gain' of the sphere and reducing overall sensitivity to low particle fluxes).

In a fourth embodiment of the invention, the fluorescence detector 14 and its associated optical filter 13 are replaced by a spectrometer capable of providing an output representative of the spectral distribution of fluorescent light emanating from the particles. Again, this would increase discrimination of biological particles in the air, but at the cost of additional complexity and manufacturing cost.

Turning now to FIGS. 2 to 4, these show a simplified low-cost bio-aerosol fluorescence sensor designed for unattended deployment in medium to large area networks surrounding vulnerable military or civilian sites. The sensor uses as the illumination source two compact xenon flash units RSL1, RSL2 to excite fluorescence in an aerosol sample volume of ~5 ml. The aerosol is drawn from the ambient environment in through inlet pipe 3' and out via outlet pipe 1' at a flow rate of 10 litres $min^{-1}$ A standard COTS absorption filter **18*a* restricts the excitation radiation from first xenon RSL1 to the UV band ~280-290 nm, optimal for exciting the biological fluorophore tryptophan, and a different absorption filter 18*b* restricts the excitation radiation from the other xenon RSL2** to ~340-380 nm, suitable for NADH.

The light from each source RSL1, RSL2 passes into the sample volume having firstly passed through the respective low pass filter **18*a*, 18*b*, where each filter is tilted at an angle (see FIG. 2) to avoid back-reflections, and then passed through a respective collimating lens 17*a*, 17*b***.

Light fluoresced from illuminated particles in the sample volume is collected by a pair of opposing spherical mirrors **15*a*, 15*b*. The sample volume is defined between the opposing spherical mirrors 15*a*, 15*b*, each mirror 15*a*, 15*b* having a central aperture 16*a*, 16*b*, whereby light collected by one mirror may be directed and passed out through the center of the other mirror to a respective detector FL1, FL2 lying behind the center of the mirror 15*a*, 15*b***.

Figure 2:
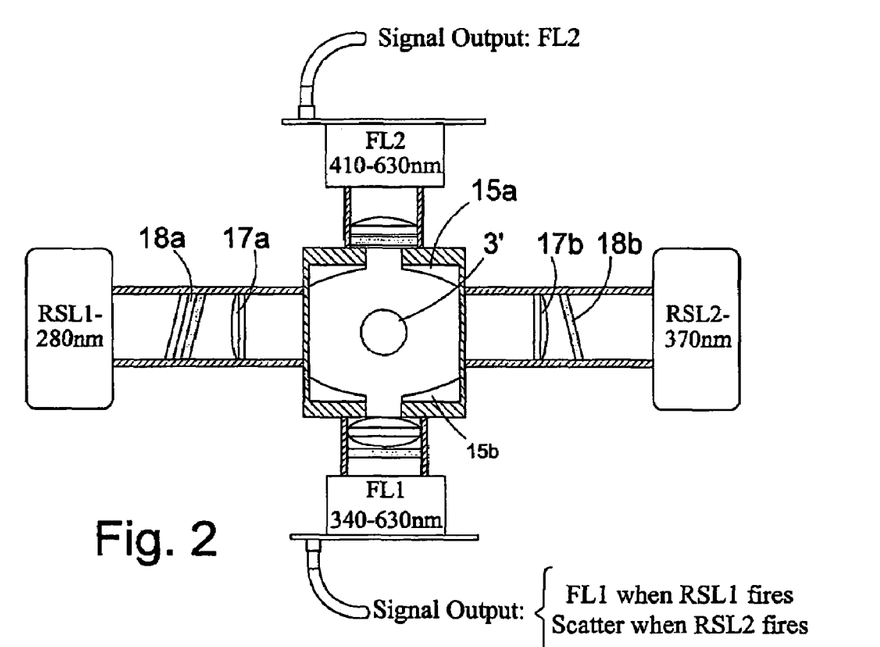
FIG. 2 is a part-sectional schematic diagram from a view similar to FIG. 1.
Figure 3:
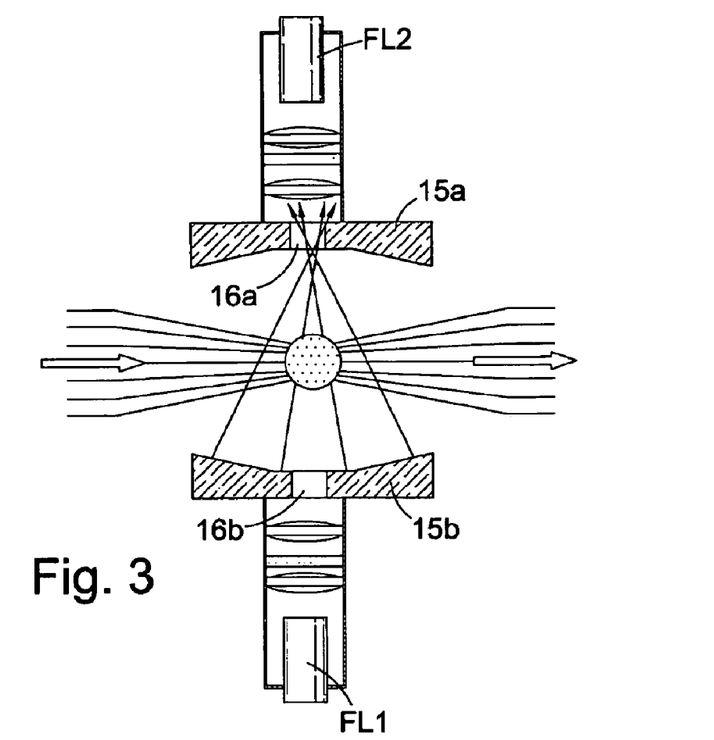
FIG. 3 is a simple schematic diagram showing the collection of fluorescent signals in the apparatus from a fluid flowing through the zone.
Figure 4:
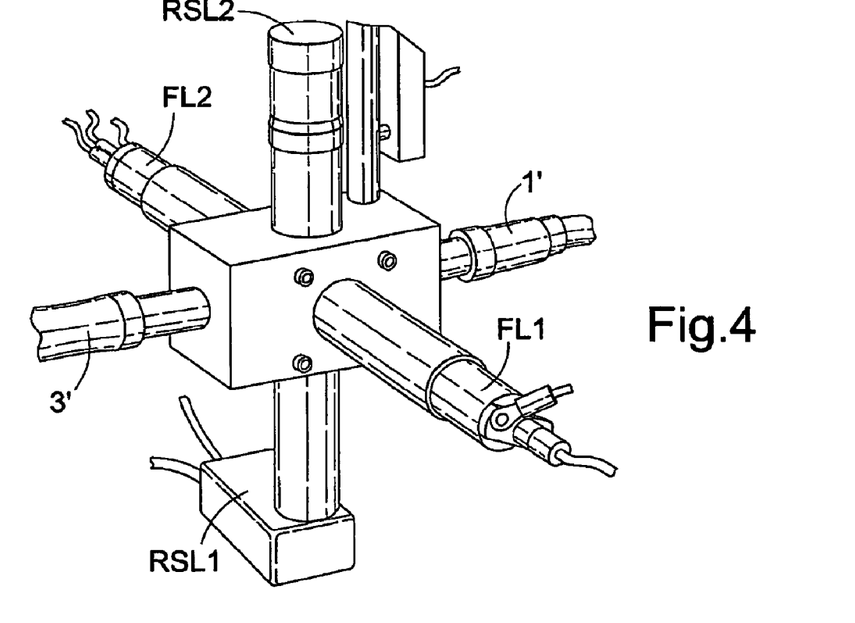
FIG. 4 is a perspective view of the apparatus.
Figure 5A:
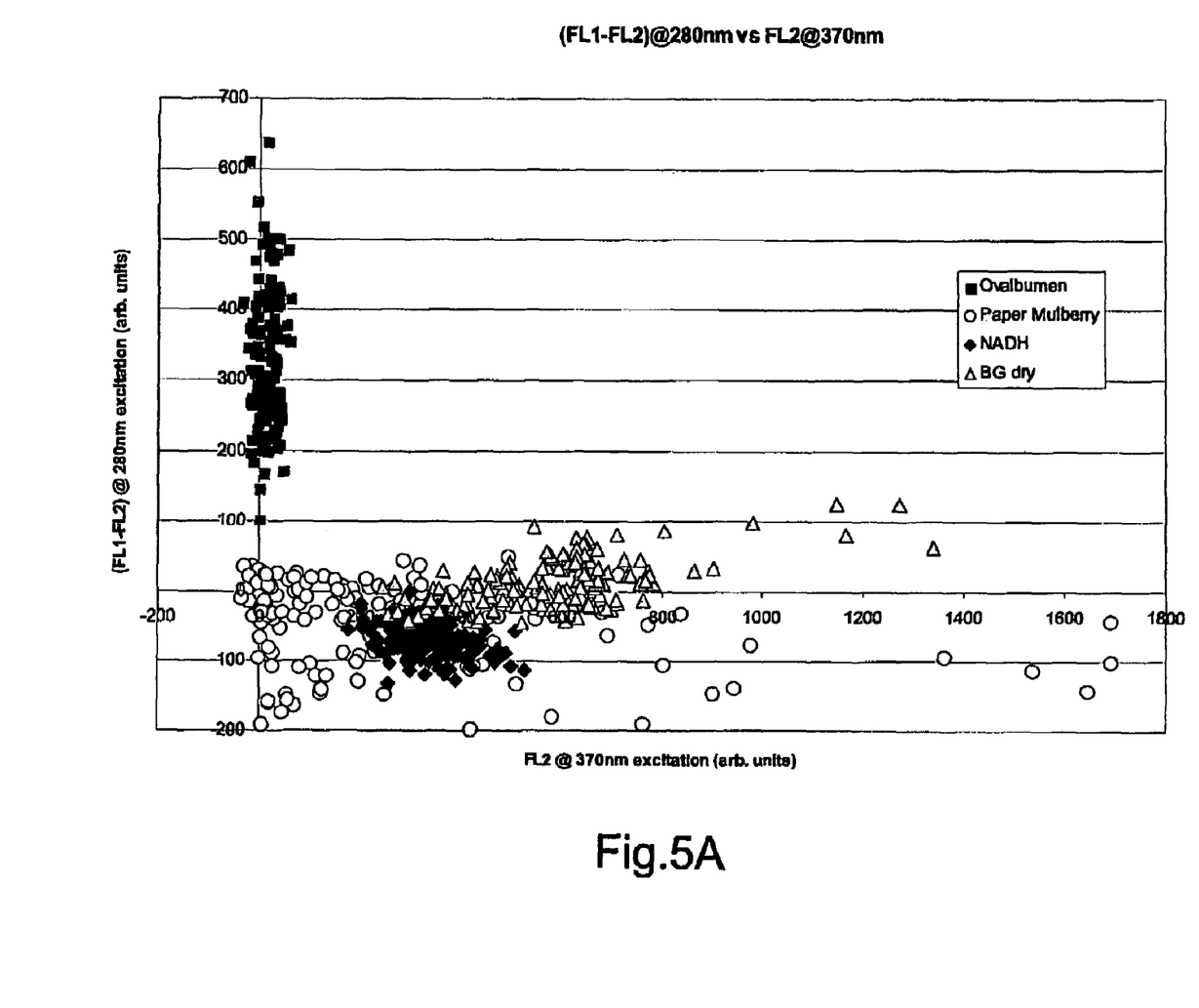
FIGS. 5a and 5b are graphs showing experimental results from use of the apparatus.
Figure 5B:
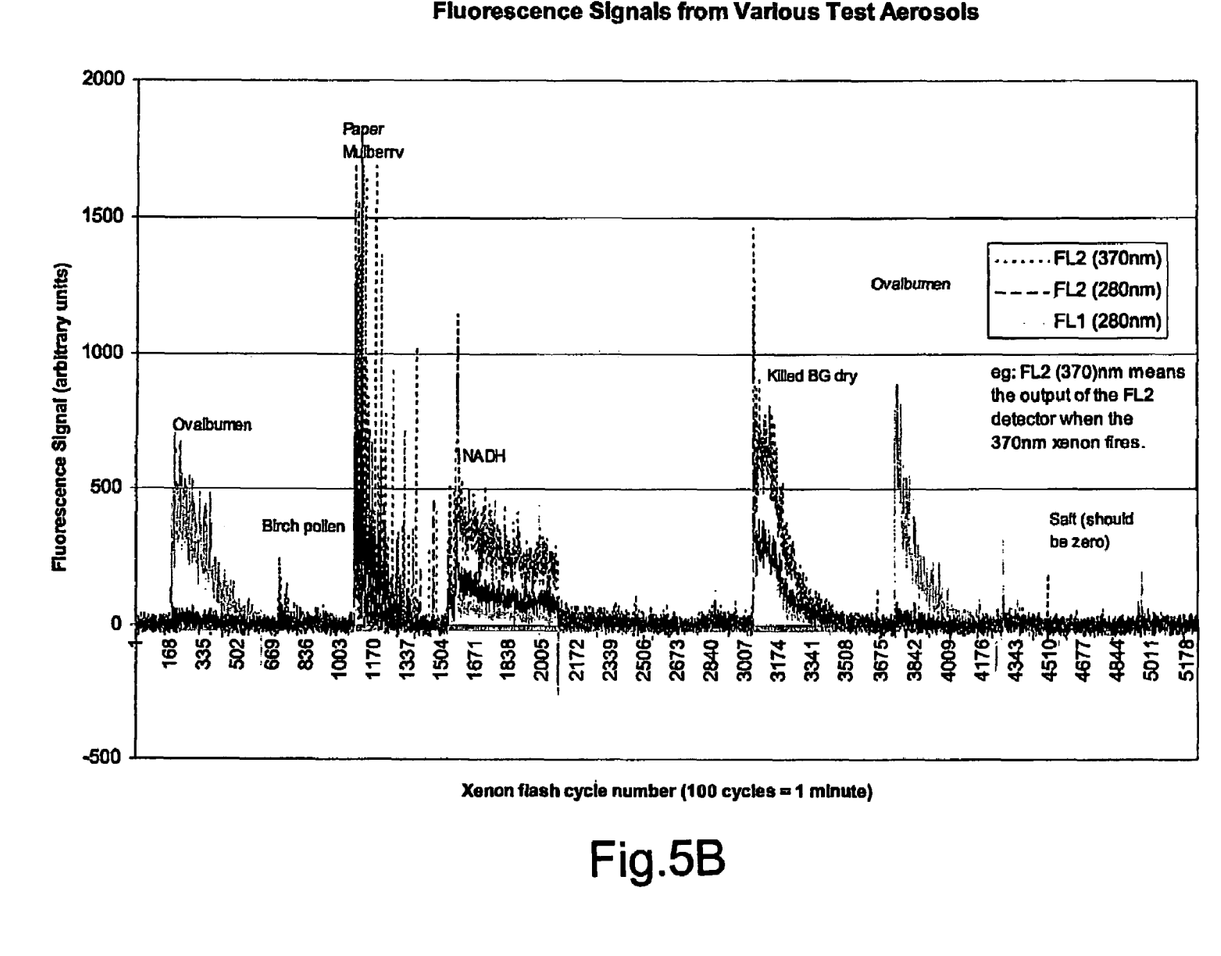

Aerosol fluorescence is measured using by the two miniature photomultiplier detectors FL1, FL2 optically filtered for one to detect radiation in the band ~340-600 nm and the other to detect radiation in the band ~410-600 nm. The second of these bands covers the principal emission from NADH, whilst the difference between the first and second detector channels (FL1-FL2) yields fluorescence in the 340-410 nm band, covering much of the tryptophan emission spectrum.

In operation, the xenons RSL1,RSL2 are pulsed alternately at 300 ms intervals. When the 260-290 nm xenon RSL1 is pulsed, the fluorescence channels FL1,FL2 record aerosol fluorescence data in the bands specified above. Conversely, when the 340-380 nm xenon RSL2 is pulsed, the first detector channel FL1 records the elastic scatter from the aerosol rather than fluorescence since its transmission (340-600 nm) encompasses the wavelength band of the excitation radiation. The second detector channel FL2 again records fluorescence in the 410-600 nm band. The excitation-emission matrix thus recorded provides data from which an estimate of the potential biological content of the aerosol may be estimated.

Referring to FIGS. 5*a* and 5*b*, these are graphs showing experimental results from use of the apparatus. FIG. 5*a* is a graph of fluorescence signal strength from each of the two different wavelength bandwidth detectors (FL1 and FL2), over an approximately one hour period during which different aerosol samples are passed through the apparatus. The graph shows superimposed plots for: (a) fluorescence signals sensed during the operation of the first xenon light source element RSL1 emitting via filter 18*a* the wavelength band of 280 nanometers average; and (b) fluorescence signals sensed for the second xenon light source element RSL2 emitting via the filter 18*b* the wavelength band of 370 nanometers average.

FIG. 5*b* is a graph showing a plot of the difference of signals from the two different fluorescent signal detection lines (FL1-FL2) as correspond to exciting irradiation at 280 nanometers plotted against the sensed fluorescent signal FL2 taken during the 370 nanometer irradiation of particles in the zone. It will be seen that by using the ratio of detected fluorescent signals at different excitation wavelengths the ability of the relatively simple low cost apparatus to discriminate different types of biological particle is significantly enhanced.

Whilst each sensor is limited in specificity, both by the use of broad spectral fluorescence bands and by multiple-particle illumination, the low unit sensor cost (<$5k) offers potential for deployment of many such sensors in large networks that would be prohibitively expensive using prior sensors or sensors based on LV laser-induced particle fluorescence.

The invention claimed is:

1. An apparatus for the detection of fluid borne particles which comprises:

a zone through which a fluid to be analyzed flows, in use;

a source of illumination to illuminate/irradiate fluid borne particles present in said zone; and a detector to detect light from the particles as an indicator of the presence or characteristics of the particles, wherein the apparatus comprises a pair of opposed concave reflective surfaces and the zone is between these surfaces, the apparatus having two sources and two detectors, the first of the two detectors detecting a first wavelength band and the second of the two detectors detecting a second wavelength band that is narrower than the first band and falls within the first band, the first source illuminating/irradiating within a wavelength band that is below the wavelength detecting band of the first detector and the second detector, and the second source illuminating/irradiating with a wavelength band that is within the wavelength detecting band of the first detector.

2. An apparatus as claimed in claim 1 wherein the first of the two detectors detects a wavelength band of about 340 to about 600 nm and the second detector detects a band of 410 to 600 nm, the first source has a wavelength band of about 260 to about 290 nm.

3. An apparatus as claimed in claim 1, wherein the second source has a wavelength band of about 340 to about 380 nm.

4. An apparatus as claimed in claim 3, wherein the first and second detectors are arranged along a first axis and the first and second source are arranged along a second axis substantially orthogonal to the first axis and the fluid flow is along a third axis substantially orthogonal to the first and second axes.

5. An apparatus as claimed in claim 1, wherein the apparatus comprises a pair of opposed concave reflective surfaces and the zone is between these surfaces.

6. An apparatus for the detection of particles as claimed in claim 5, wherein each of the pair of opposed substantially concave reflective surfaces comprises a respective discrete mirror.

7. An apparatus for the detection of particles as claimed in claim 5, wherein the apparatus comprises an integrating sphere and the pair of opposed concave reflective surfaces are reflective surfaces of the integrating sphere.

8. An apparatus for the detection of particles as claimed in claim 1, wherein the fluid to be analyzed flows through the zone along a flow path and the illuminations irradiation source is directed along the flow path.

9. An apparatus for the detection of particles as claimed in claim 8 as dependent on claim 7, wherein the illumination/irradiation and the fluid enter the integrating sphere by a common aperture.

10. An apparatus for the detection of particles as claimed in claim 1, having an integrating sphere and wherein the fluid is constrained to flow through a transparent tube extending through the zone and which extends along the diameter of the integrating sphere.

11. An apparatus for the detection of particles as claimed in claim 10, wherein the apparatus further comprises an optically absorbing beam-dump at the distal end of the tube to absorb the illumination/irradiation beam.

12. An apparatus for the detection of particles as claimed in claim 10, wherein the illumination/irradiation is directed along the tube as a beam and the diameter of the beam is such that the beam fills most of the tube without coming into contact with the tube walls.

13. An apparatus for the detection of particles as claimed in claim 10, wherein the apparatus incorporates a detector at the distal end of the tube to measure the power of the illumination/irradiation beam.

14. An apparatus for the detection of particles as claimed in claim 1, wherein the source is a pulsed light source.

15. An apparatus for the detection of fluid borne biological particles as claimed in claim 1, the apparatus being adapted for the detection of fluid borne biological particles, wherein the source of illumination serves to illuminate/irradiate fluid borne particles present in said zone and to excite the particles to fluoresce, and the apparatus has a detector to detect fluorescence from the particles as an indicator of the presence of biological particles, wherein the sphere has an optical detector at a detecting aperture in the sphere for sensing fluorescence radiation, the optical detector having a spectrometer or a number of different filters that are selectable between to enable a range of different wavelength bands to be monitored.

16. An apparatus for the detection of fluid borne biological particles as claimed in claim 1, wherein the apparatus further comprises a fan as the means to cause airflow through the zone.

17. An apparatus for the detection of fluid borne biological particles as claimed in claim 5, wherein each mirror is of substantially spherically concave type and the pair are substantially coaxially opposed to each other.

18. An apparatus for the detection of fluid borne biological particles as claimed in claim 5, wherein each respective substantially spherically concave mirror has a central aperture and has a respective detector to detect light received through the aperture from the other mirror.

19. An apparatus for the detection of fluid borne biological particles as claimed in claim 17, wherein the axis linking the centers of the opposed substantially spherically concave mirrors is substantially orthogonal to an axis of illumination from the source of illumination.

20. An apparatus for the detection of fluid borne biological particles as claimed in claim 1, wherein the apparatus has two or more different sources of illumination.

21. An apparatus for the detection of fluid borne biological particles as claimed in claim 20, wherein the at least two sources of illumination comprise two xenon sources each emitting a different wavelength band of light to the other.

22. An apparatus for the detection of fluid borne biological particles as claimed in claim 20, wherein the different light sources are spatially distinct from each other.

23. An apparatus for the detection of fluid borne biological particles as claimed in claim 20, wherein the apparatus has a single light source element and which is switchable between different wavelength bands of emission.

24. An apparatus for the detection of fluid borne biological particles as claimed in claim 23, wherein the light source element(s) is/are xenon light source elements having a low pass filter between the source and the zone to allow only the lower wavelengths that are in the appropriate range to excite fluorescence to pass.

25. An apparatus for the detection of fluid borne biological particles as claimed in claim 24, wherein the filter only allows radiation at or under about 370 nanometers to pass.

26. An apparatus for the detection of fluid borne biological particles as claimed in claim 20, wherein there are two xenon light source elements and each has a different respective filter.

27. An apparatus for the detection of fluid borne biological particles as claimed in claim 26, wherein one light source element/filter combination emits light up to about 290 nanometers and the other emits light from above 290 nanometers 28. An apparatus for the detection of fluid borne biological particles as claimed in claim 27, wherein the other light source element/filter combination emits light from above 290 nanometers to about 380 nanometers 29. An apparatus for the detection of fluid borne biological particles as claimed in claim 20 as dependent on claim 18, wherein the two spatially discrete light sources are spaced apart in a configuration each along an axis wherein the axis is substantially orthogonal to an axis linking the detectors.

30. An apparatus for the detection of fluid borne biological particles as claimed in claim 18, wherein an axis linking the detectors is substantially aligned with an axis linking the centers of each of the opposed spherical mirrors.

31. An apparatus for the detection of fluid borne biological particles as claimed in claim 20, wherein the apparatus further comprises a processor configured to operate the apparatus in a manner whereby the source of illumination alternately changes between two or more different band widths of wavelength.

32. An apparatus for the detection of fluid borne biological particles as claimed in claim 31, wherein the processor is further programmed to process signals sensed from the one or more detectors to provide a ratio of sensed signal for one wavelength or wavelength band of illuminating light relative to sensed signal for a different wavelength or band of wavelength of illuminating light.

33. An apparatus for the detection of fluid borne biological particles as claimed in claim 32, wherein the processor is programmed to process signals sensed from the one or more detectors to provide a ratio of sensed signal for one wavelength or wavelength band of illuminating light relative to sensed signal for a different wavelength or band of wavelength of illuminating light at each of two or more different sensed wavelengths or bands of wavelength of detected fluorescence signal.

34. An apparatus for the detection of fluid borne biological particles as claimed in claim 1, wherein the apparatus has two or more detectors each with a different wavelength pass/bandpass.

* * * * *